US011963754B2

(12) United States Patent
Dispenza et al.

(10) Patent No.: US 11,963,754 B2
(45) Date of Patent: Apr. 23, 2024

(54) ACCELERATED ACQUISITION OF SCAN DATA BY MEANS OF MAGNETIC RESONANCE

(71) Applicant: Siemens Healthcare GmbH, Erlangen (DE)

(72) Inventors: Nadine Dispenza, Erlangen (DE); Ralf Kartaeusch, Bubenreuth (DE); Dominik Paul, Bubenreuth (DE); Manuel Stich, Parkstein (DE); Mario Zeller, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 377 days.

(21) Appl. No.: 17/038,810

(22) Filed: Sep. 30, 2020

(65) Prior Publication Data

US 2021/0093222 A1 Apr. 1, 2021

(30) Foreign Application Priority Data

Sep. 30, 2019 (EP) .................................... 19200322

(51) Int. Cl.
*A61B 5/06* (2006.01)
*G01R 33/56* (2006.01)
*G06T 7/00* (2017.01)

(52) U.S. Cl.
CPC .......... *A61B 5/062* (2013.01); *G01R 33/5608* (2013.01); *G06T 7/0012* (2013.01); *G06T 2207/10088* (2013.01)

(58) Field of Classification Search
CPC ........................ A61B 5/062; G01R 33/5608; G01R 33/4824; G01R 33/4826; G01R 33/4816; G06T 7/0012; G06T 2207/10088
See application file for complete search history.

(56) References Cited

U.S. PATENT DOCUMENTS

| 2013/0076357 | A1 | 3/2013 | Grodzki et al. |
| 2013/0249549 | A1* | 9/2013 | Pfeuffer ............... G01R 33/543 324/309 |
| 2014/0084919 | A1 | 3/2014 | Johnson |
| 2014/0197834 | A1* | 7/2014 | Porter ................. G01R 33/5616 324/309 |
| 2015/0234024 | A1* | 8/2015 | Grodzki ............. G01R 33/4824 324/309 |

(Continued)

FOREIGN PATENT DOCUMENTS

| DE | 102010041450 A1 * | 3/2012 | ......... G01R 33/4816 |
| DE | 102011083619 A1 | 3/2013 | |
| DE | 102013201616 B3 * | 7/2014 | ......... G01R 33/4835 |

OTHER PUBLICATIONS

Setsompop, Kawin et al. "Blipped-Controlled Aliasing in Parallel Imaging for Simultaneous Multislice Echo Planar Imaging with Reduced g-Factor Penalty" Magnetic Resonance in Medicine, vol. 67, pp. 1210-1224, 2012 (first published online 2011) // DOI 10.1002/mrm.23097.

(Continued)

*Primary Examiner* — Shahdeep Mohammed
*Assistant Examiner* — Fikirte (Fiki) T Ashine
(74) *Attorney, Agent, or Firm* — Banner & Witcoff Ltd.

(57) ABSTRACT

Accelerated acquisition of scan data by means of magnetic resonance to enable short echo times so that scan data of substances can also be acquired with a transversal relaxation time.

13 Claims, 5 Drawing Sheets

(56) References Cited

U.S. PATENT DOCUMENTS

2015/0253408 A1* 9/2015 Grodzki ............... G01R 33/307
324/309

OTHER PUBLICATIONS

Van Vaals, Joop J. et al. ""Keyhole" method for accelerating imaging of contrast agent uptake" Journal of Magnetic Resonance Imaging, vol. 3, No. 4, pp. 671-675, July/Aug. 1993.

Breuer, Felix A. et al. "Controlled Aliasing in Parallel Imaging Results in Higher Acceleration (CAIPIRINHA) for Multi-Slice Imaging" Magnetic Resonance in Medicine, vol. 53, No. 3, pp. 684-691, 2005 // DOI: 10.1002/mrm.20401.

Gagoski, Borjan A. et al. "RARE/Turbo Spin Echo Imaging with Simultaneous Multislice Wave-CAIPI" Magnetic Resonance in Medicine; vol. 73; pp. 929-938; 2015 // DOI: 10.1002/mrm.2561.

Chen, Feiyu et al. "Self-Calibrating Wave-Encoded Variable-Density Single-Shot Fast Spin Echo Imaging." Journal of Magnetic Resonance Imaging; 2017 // DOI: 10.1002/jmri.25853.

Weiger, Markus et al. "Short-T2 MRI: Principles and recent advances" Progress in Nuclear Magnetic Resonance Spetroscopy; vol. 114-115, pp. 237-270, 2019.

Heid, Oliver et al. "Rapid Single Point (RASP) Imaging" SMR, 3rd Annual Meeting, p. 684, 1995.

Bilgic, Berkin et al. "Wave-CAIPI for Highly Accelerated 3D Imaging" Magnetic Resonance in Medicine, vol. 73, No. 6, pp. 2152-2162, 2015 // DOI: 10.1002/mrm.25347.

Gurney, Paul T. et al. "Design and Analysis of a Practical 3D Cones Trajectory" Magnetic Resonance in Medicine, vol. 55, pp. 575-582, 2006.

Grodzki, David M. et al. "Ultrashort echo time imaging using pointwise encoding time reduction with radial acquisition (PETRA)" Magnetic Resonance in Medicie, vol. 67, pp. 510-518, Jun. 30, 2011 // DOI: 10.1002/mrm.23017.

Nielles-Vallespin Sonia et al. "3D Radial Projection Technique with Ultrashort Echo Times for Sodium MRI: Clinical Applications in Human Brain and Skeletal Muscle" Magnetic Resonance in Medicine, vol. 57, pp. 74-81, 2007 // DOI: 10.1002/mrm.21104.

Cauley, Stephen F. et al. "Autocalibrated Wave-CAIPI Reconstruction; Joint Optimization of k-Space Trajectory and Parallel Imaging Reconstruction" Magnetic Resonance in Medicine, vol. 78, No. 3, pp. 1093-1099, 2016 // DOI: 10.1002/mrm.26499.

Irarrazabal, Pablo et al. "Fast Three Dimensional Magnetic Resonance Imaging" Magnetic Resonance in Medicine, vol. 33, pp. 656-662, 1995.

Kim, Tae Hyung et al.: "Wave-LORAKS for faster Wave-CAIPI MRI" SMRM—2017; Proc. Intl. Soc. Mag. Reson. Med. 25; 2017.

European Search Report dated Mar. 11, 2020 for European Patent Application No. 19200322.6.

* cited by examiner

ACCELERATED ACQUISITION OF SCAN DATA BY MEANS OF MAGNETIC RESONANCE

TECHNICAL FIELD

The disclosure relates to an accelerated acquisition of scan data by means of magnetic resonance, which enables in particular particularly short echo times TE (e.g. TE<500 µs) so that scan data of substances can also be acquired with a transversal relaxation time T2 in a range of 30-80 µs, such as bones, for instance.

BACKGROUND

Magnetic resonance technology (hereinafter, the abbreviation MR stands for magnetic resonance) is a known technology with which images of the interior of an examination object can be produced. In simple terms, this is done by placing the examination object in a magnetic resonance apparatus in a comparatively strong static, homogeneous main magnetic field, also called the $B_0$ field, at field strengths of 0.2 Tesla to 7 Tesla and higher, with the result that the nuclear spins of the examination object are oriented along the main magnetic field. Radiofrequency excitation pulses (RF pulses) are radiated into the examination object in order to induce nuclear spin resonances which can be measured as signals, the induced nuclear spin resonances are measured as what is known as k-space data, and this data is used as the basis for reconstructing MR images or obtaining spectroscopic data. For position encoding of the scan data, rapidly switched magnetic gradient fields, abbreviated to gradients, are overlaid on the main magnetic field. The scan data recorded is digitized and stored as complex numerical values in a k-space matrix. From the k-space matrix loaded with values, an associated MR image is reconstructable, for example, by means of a multi-dimensional Fourier transform.

A favored pulse sequence for exciting and recording nuclear spin resonances is what is known as gradient echo sequence (GRE sequence), in particular for recording three-dimensional (3D) data sets. However, such GRE-based MR examinations are in most cases very loud and therefore unpleasant for a patient to be examined. The main reason for the high noise development are the gradient constellations which change rapidly in terms of time during GRE sequences and the high slew rates (temporal change in the gradient amplitudes (dG/dt) associated therewith. Moreover, parameters which require particularly rapid switching of the gradients, such as, for instance, short echo times or gradient spoiling, are often required in the protocol of the sequence.

By acquiring MR data with very short echo times TE (e.g. TE<500 µs), new application areas are offered in magnetic resonance tomography. As a result, it is possible to represent substances or tissues which cannot be represented by means of conventional sequences, such as e.g. a (T) SE sequence ("(Turbo) Spin Echo") or a GRE sequence, since their T2 time, the relaxation of the transverse magnetization of this substance or tissue, is significantly shorter than the shortest echo time TE which can be achieved there and thus a corresponding signal of these substances or tissues has already decayed at the recording time. With echo times which lie in the region of the corresponding decay time, it would be possible, for instance, to represent bones, teeth or ice in an MR image, although the T2 time of these objects lies in a range of 30-80 µs.

According to the prior art, sequences which enable a very short echo time are already known. One example is the radial UTE sequence ("Ultrashort Echo Time"), such as is described e.g. in the article by Sonia Nielles-Vallespin "3D radial projection technique with ultrashort echo times for sodium MRI: Clinical applications in human brain and skeletal muscle", Magn. Res. Med. 2007; 57; pp. 74-81. With this sequence type, following a waiting time T_delay after a non-slice-selective or slice-selective excitation, the gradients are accelerated and started at the same time as the data acquisition. The k-space trajectory scanned in this way after an excitation runs radially outward from the k-space center. This raw data must therefore firstly be recalculated on a Cartesian k-space grid, e.g. by means of regridding, before reconstruction of the image data from the raw data recorded in the k-space by means of Fourier transform.

A further approach to enabling short echo times is to scan the k-space in a pointwise manner, by the free induction decay (FID) being acquired. Such a method is also referred to as single point imaging, since only one raw data point in the k-space is essentially acquired per RF excitation. One example of such a method for single point imaging is the RASP method ("Rapid Single Point (RASP) Imaging", O. Heid, M. Deimling, SMR, 3rd Annual Meeting, pp. 684, 1995). According to the RASP method a raw data point is read out in the k-space, the phase of which was encoded by the gradients, at a fixed point in time after the RF excitation by an RF excitation pulse relating to the "echo time" TE. The gradients are changed by means of the magnetic resonance system for each raw data point or scan point and the k-space is thus scanned point by point.

Grodzki et al. describe in "Ultrashort echo time imaging using pointwise encoding time reduction with radial acquisition (PETRA)", Magn. Reson Med. 2012 February; 67 (2):510-8 a method which combines the cited UTE method and a single point imaging method, such as e.g. a RASP method. The PETRA sequence has the further advantage of, conversely to other pulse sequences (in particular compared with GRE sequences), resulting in a particularly minimal noise load, which is very unpleasant for examined patients. Here, the duration of the data acquisition which accompanies the acquisition scheme does not make it possible to map dynamic procedures, such as e.g. a contrast agent injection. With the typical scan time of a PETRA acquisition of several minutes, a contrast agent is already distributed homogenously in the body, before the measurement is concluded, so that with the attempt to map a contrast agent injection, only unspecific mixed contrasts can be achieved.

The desire for ever faster MR recordings in the clinical environment leads on the other hand to a resurgence in methods in which a plurality of images are recorded simultaneously. In general, these methods can be characterized in that at least during a part of the scan, transverse magnetization of at least two slices is used simultaneously in a targeted manner for the imaging process ("multi-slice imaging", "slice multiplexing" or "simultaneous multi-slice" (SMS)). Contrary hereto, with the established "multi-slice imaging", the signal of at least two slices is recorded alternately, e.g. completely independently of one another with a correspondingly longer scan time.

Known SMS methods are methods, for instance, which employ methods from the parallel imaging (ppa), in which knowledge about the sensitivity distribution of the receive coils used in the acquisition of scan data is used as additional information, in order to fulfill scan data which is underscanned in accordance with Nyquist, in the slice direction, in order to separate signals recorded overlaid from several slices into signals of the individual slices. The latter methods also include, for example, the CAIPIRINHA technique as described by Breuer et al. in "Controlled Aliasing in Parallel Imaging Results in Higher Acceleration (CAIPIRINHA) for Multi-Slice Imaging", Magnetic Resonance in Medicine 53, 2005, pp. 684-691 and the blipped CAIPIRINHA technique as described by Setsompop et al. in "Blipped-Controlled Aliasing in Parallel Imaging for Simultaneous Multislice Echo Planar Imaging With Reduced g-Factor Penalty", Magnetic Resonance in Medicine 67, 2012, pp. 1210-1224, wherein the g-factor ("g-factor", short for "geometry factor") used in the last-mentioned title represents a measure of a separability of the various receive coils used.

As a method of further reducing this g-factor, it is further known for CAIPIRINHA methods to change the read-out trajectories in the k-space, and thus the acquisition scheme, so that the scan data is acquired along read-out trajectories which run in a wavelike or helical manner. This is described, for instance, in the article by Bilgic et al "Wave-CAIPI for Highly Accelerated 3D Imaging", Magnetic Resonance in Medicine 73:2152-2162 (2015), or for two-dimensional (2D) imaging in Chen et al. "Self-Calibrating Wave-Encoded Variable-Density Single-Shot Fast Spin Echo Imaging", J. Magn. Reson. Imaging 2018; 47:954-966, or also for spin echo (SE) methods in GAGOSKI et al. "RARE/Turbo Spin Echo Imaging with Simultaneous Multislice Wave-CAIPI", Magn. Reson. Med. 73:929-938 (2015).

SUMMARY

An object underlying the disclosure is to enable an accelerated acquisition of scan data by means of magnetic resonance, which allows in particular particularly short echo times TE (e.g. TE<500 µs), so that scan data of substances with a transversal relaxation time T2 in a range of 30-80 µs such as e.g. bones, can also be acquired in a clinically acceptable scan time.

The object is achieved by a method for producing scan data of an examination object by means of magnetic resonance technology as claimed in claim 1, by a magnetic resonance system as claimed in claim 11, by a computer program as claimed in claim 12, and by an electronically readable data storage medium as claimed in claim 13.

A method for producing scan data of an examination object by means of magnetic resonance technology comprises the following steps:

reading out a k-space corresponding to the imaging area, comprising the steps:
a) switching a constant gradient ($G_x$) by means of a gradient unit of a magnetic resonance system,
b) radiating an RF excitation pulse by means of an RF transmit-receive device of the magnetic resonance system,
c) following a time t1 after the last irradiated RF excitation pulse, recording echo signals by means of the RF transmit-receive device,
d) storing the recorded echo signals as scan data along the k-space trajectory predetermined by the strength of the switched gradients,
wherein the steps a) to d) are carried out repeatedly with varyingly switched constant gradients ($G_x$), wherein the various gradients are switched in at least two phase encoding directions, and wherein at least once following the time t1 after the last switched RF excitation pulse, additional gradients with a modulating amplitude are switched in at least one direction which is orientated at right angles to a direction predetermined by the already switched constant gradient,
until the k-space corresponding to the mapping area is read out in a first region (B1) which depends on the time t1,
e) reading out the k-space, corresponding to the mapping area, which is not covered by the first region (B1) of the k-space (B2) and which comprises at least the k-space center, in a different way to that described by steps a) to d), and storing this scan data,
reconstructing image data from the recorded scan data of the k-space by means of a control facility of the magnetic resonance system.

By switching additional gradients with a modulating amplitude during a recording of scan data, coverage of the k-space is increased during the recording of the scan data. As a result, fewer repetitions of recordings of scan data are required overall, in order to scan a desired k-space in a desired coverage than without the additional gradients. Scan time can be saved in this way.

A magnetic resonance system comprises a magnet unit, a gradient unit, a radio frequency unit and a control facility embodied to carry out a method with an additional gradient unit.

A computer program implements a method on a control facility if it is executed on the control facility.

In this regard the computer program can also be present in the form of a computer program product which is directly loadable into a memory store of a control facility, having program code means in order to implement a method when the computer program product is executed in the computer unit of the computer system.

An electronically readable data storage medium comprises electronically readable control information stored thereupon, which comprises at least one computer program and is configured so that it carries out a method when the data storage medium is used in a control facility of a magnetic resonance system.

The advantages and embodiments specified in respect of the method also apply similarly to the magnetic resonance system, the computer program product and the electronically readable data storage medium.

BRIEF DESCRIPTION OF THE DRAWINGS

Further advantages and details of the present disclosure are disclosed in the following description of exemplary embodiments and by reference to the drawings. The examples given do not represent restrictions of the disclosure. In the drawings.

DETAILED DESCRIPTION

Figure 1:
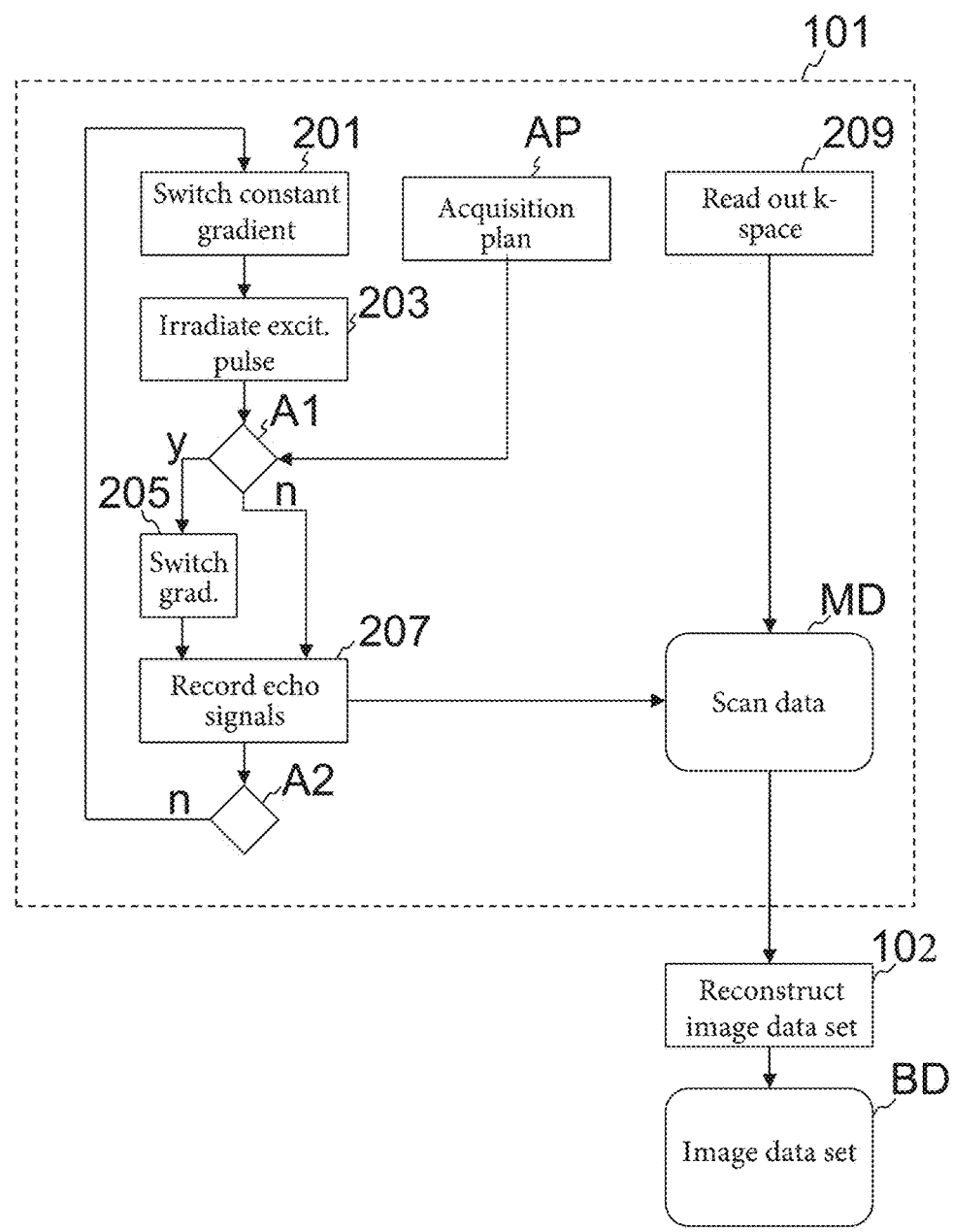
FIG. 1 shows a schematic flow chart of a method in accordance with aspects of the disclosure.

FIG. 1 shows a schematic flow chart of a method for producing scan data of an examination object by means of magnetic resonance technology.

In this regard a k-space corresponding to the mapping area is read out in a first step 101 for producing an image data set.

To this end, a constant gradient is switched (block 201) by means of a gradient unit of a magnetic resonance system in a gradient direction $G_r$ (which differs for varying repetitions), and a, in particular non-slice-selective HF excitation pulse is irradiated by means of an RF transmit-receive device of the magnetic resonance system (block 203). If the HF excitation pulse is non-slice-selective, a three-dimensional volume can be scanned in the k-space since the excitation is not restricted to one slice. In this regard the irradiated RF excitation pulses are irradiated for instance only after reaching the full strength of the constant gradient. As a result, a noise formation caused by the gradients can be significantly reduced.

A query A1 is used to decide whether additional gradients are switched for the previously (in block 201) switched constant gradient. If this is not the case (A1, "n"), block 207 is continued.

Additional gradients are to be switched (A1, "y") at least once, however, after a previously (in block 201) switched constant gradient, so that additional gradients with a modulating amplitude are switched in at least one direction which is orientated at right angles to a direction which is predetermined by the already switched constant gradient (block 205) for one such previously (in block 201) switched constant gradient following time t1 after the last switched HR excitation pulse.

The constant gradients $G_r$ for which additional gradients are to be switched, and if so which additional gradients, can be defined in a recallable manner in an acquisition plan AP.

In this regard, a maximum amplitude of a modulation and/or a curve of an amplitude development of the modulation can be selected, for instance, in a fixedly stored manner by a user or for specific applications in each case in the direction $k_x$, which corresponds to the constant gradient $G_x$, in the k-space of additional gradients to be switched, e.g. as a function of a desired coverage of the k-space and/or a selected permissible noise development. For instance, it is conceivable to allow an amplitude to increase at an increasing distance from the k-space center, in order to obtain a helical k-space trajectory which runs on a cone section of the k-space. In this regard the increase in amplitude can be increased e.g. linearly, exponentially or according to a tangent function or another suitable function with a distance of a k-space point from the k-space center which is scanned according to the switched gradients. With an amplitude which is increased in this way with an increasing distance from the k-space center, the coverage of the k-space scanned by the corresponding cone-shaped k-space trajectories can be improved.

Examples of amplitudes increasing with the distance from the k-space center having k-space trajectories running in particular in conical sections, are described e.g. in the article by Gurney et al. "Design and analysis of a practical 3D cones trajectory", Magn. Res. Med. 2006; 55; pp. 575-582 or already in the article by Irarrazabal et al. "Fast Three Dimensional Magnetic Resonance Imaging", Magn. Res. Med. 1995; 33; pp. 656-662.

Furthermore, a portion of the first region can be predetermined, in which additional gradients are switched when scan data is recorded. The greater the portion of the first region, in which additional gradients are switched with a recording of scan data, the fewer different constant gradients and thus fewer repetitions of the blocks 201 to 207 are required for a desired coverage of the k-space in the first region. The overall scan time can thus be shortened accordingly. It can also be selected that additional gradients are switched in the entire first region, in other words in a portion of 100% of the first region. However, a noise formation as a result of eddy currents is increased again by the additional gradients so that it may be useful (if necessary as a function of a maximum amplitude of the modulation of the additional gradients) to specify a maximum portion in which additional gradients are switched when scan data is recorded.

The portion of the first region, in which additional gradients are switched when scan data is recorded, can therefore be defined as a function of a permitted noise development and/or as a function of a desired maximum scan time for the recording of all scan data of the first region and/or as a function of a desired k-space coverage.

In any case, following a time t1 after the last irradiated RF excitation pulse, echo signals are recorded by means of the RF transmit-receive device and stored (block 207) as scan data MD along the k-space trajectory predetermined by the strength and direction of the gradients switched (in block 201 and possibly block 205).

Since all desired echo signals are recorded as scan data MD after an HF excitation pulse and the corresponding k-space trajectory is thus read out, in query A2 a check is carried out to determine whether or not the k-space corresponding to the mapping area is already read out in a first region which depends on the time t1. If no ("n"), a renewed repetition is started in block 201, wherein with each repetition various constant gradients are switched in in each case another direction in block 201.

The k-space which corresponds to the mapping area and which is not covered by the first region of the k-space, which first region is scanned by means of blocks 201 to 207, is read out at any point in time or also at various points in time before, between or after reading out the k-space trajectories filling the first region e.g. point by point by means of a single point imaging method, such as e.g. RASP or in another known way, (block 209) and is likewise stored as scan data MD. If the scan data, which contains the k-space center, is acquired in a Cartesian manner in this way, a so-called regridding is superfluous before the reconstruction of image data.

When the k-space corresponding to the mapping area is read out, the constant gradients between the irradiation of a first HF excitation pulse for recording scan data of the k-space corresponding to the mapping area and a second HF excitation pulse for recording further scan data of the k-space corresponding to the mapping area can be changed continuously. I.e. the constant gradients are not shut down after each recording of a k-space trajectory and are booted up again for the recording of the next k-space trajectory, but the constant gradients are only shut down or booted up from the already received strength until the strength required for the next recording is reached. Therefore eddy currents induced by the current feed of the gradient unit required to generate the constant gradients can be reduced; this reduces the formation of noises which are caused by the forces which the eddy currents exert on the gradient unit.

In particular, it is advantageous in this regard to arrange the k-space trajectories to be read out so that the strength of the constant gradients in each case only has to be changed as little as possible, as a result of which the noises caused by the change in the various constant gradients can be further reduced.

In a further step 102, an image data set BD can be reconstructed from the recorded echo signals which are stored as scan data MD, e.g. by means of the control facility of the magnetic resonance system, using a Fourier transform and possibly using regridding methods, said image data set BD being stored and/or shown in a similar manner to the scan data MD.

Figure 2:
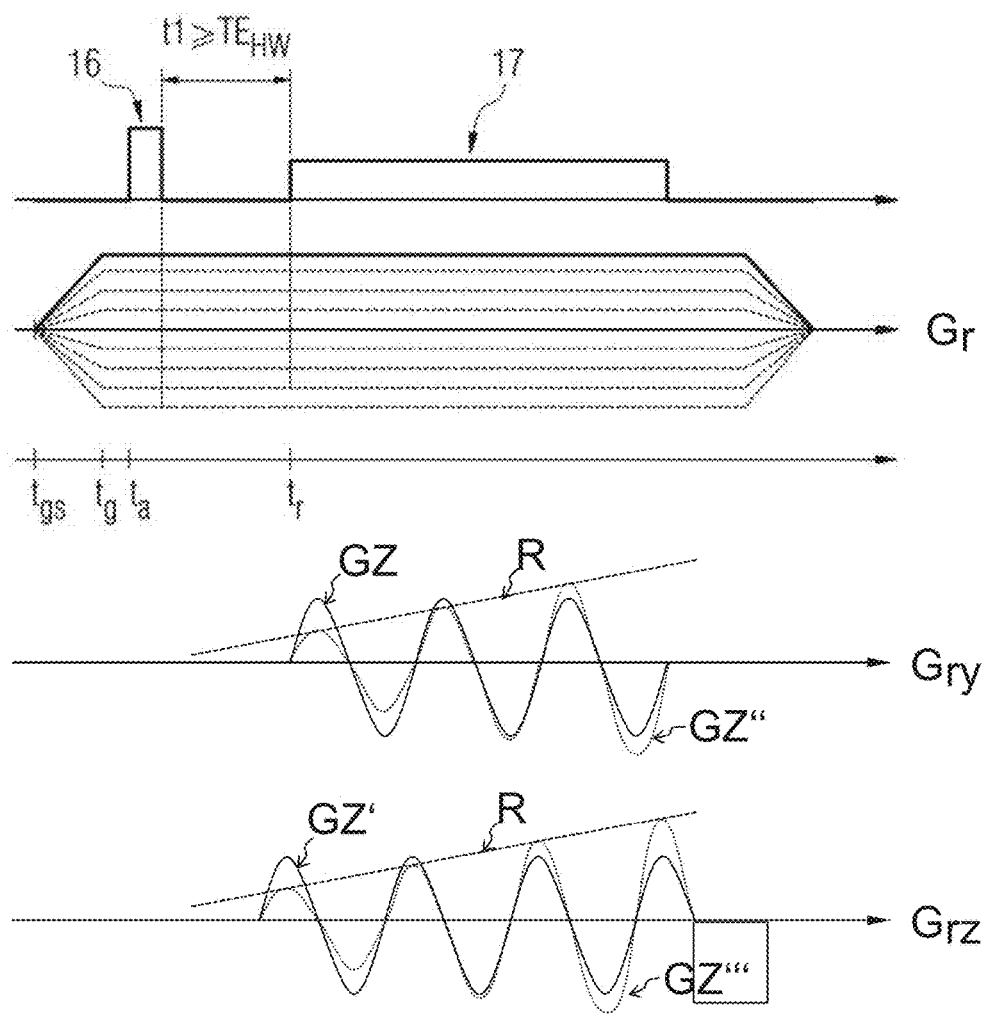
FIG. 2 shows a schematic representation of a part of a sequence for acquiring scan data in accordance with aspects of the disclosure.

FIG. 2 shows a schematic representation of part of a sequence, which can be used to acquire scan data in a first region (cf. FIG. 1, blocks 201 to 205 or 207). At a point in time $t_{gs}$ a gradient for phase encoding in the gradient direction $G_r$ is booted up, wherein the gradient direction is produced from the directions (e.g. at least two phase encoding directions Gx, Gy, Gz), in which the gradient is switched, and at a point in time $t_g$ reaches its full strength, which is kept constant. An HF excitation pulse 16 is irradiated at a subsequent point in time $t_a > t_g$. Following an echo time t1 after the HF excitation pulse 16, which e.g. for ultrashort echo times, corresponds to the hardware minimal switchover time between a transmit mode and a receive mode of a used HF transmit-receive device $TE_{HW}$, a read out time period 17 for reading out the echo signals and thus for recording scan data is begun at time instant $t_r$.

In the exemplary embodiment shown in FIG. 2, the constant gradient is irradiated switched in the phase encoding direction before the HF excitation pulse 16.

Additional gradients with a modulating amplitude GZ, GZ', GZ", GZ''' can be switched e.g. in at least one direction $G_{ry}$ and/or $G_{rz}$ at right angles to the gradient direction Gr, wherein the directions $G_{ry}$ and $G_{rz}$ are each at right angles to one another. Additional gradients GZ, GZ', GZ", GZ''' are switched so that they act in the read-out time period 17, during the recording of the scan data.

Of the additional gradients GZ, GZ', GZ" and GZ''' shown by way of example in FIG. 2, the additional gradients GZ and GZ' only have one, e.g. sinusoidal or cosinusoidal, modulation of their amplitude A, so that $k_{ry}(t) = A_{max} * \sin(\overline{\omega}t)$ applies, for instance for GZ in the $G_{ry}$ direction, and $k_{rz}(t) = A_{max} * \cos(\overline{\omega}t)$ applies for GZ' in $G_{rz}$ direction, for instance; $A_{max}$ equates to the respective maximum amplitude.

The additional gradients GZ" and GZ''' shown, in addition to a modulation, have an increase R in their amplitude A which increases with an increasing distance from the k-space center, so that, for instance, $k_{ry}(t) = R * A_{max} * \sin(\overline{\omega}t)$ applies for GZ" in $G_{ry}$-direction and $k_{rz}(t) = R * A_{max} * \cos(\overline{\omega}t)$ applies for GZ''' in $G_{rz}$-direction for instance; again $A_{max}$ equates to the respective maximum amplitude, and R equates to the selected increase (R=R(d)) which is dependent on the distance d from the k-space center. The distance d from the k-space center increases in accordance with the gradient $G_r$ with the time t(d=d(t)).

The increase R(d(t)) can be increased with the distance d from the k-space center e.g. linearly (R(d)=c*d, with c of a constant), corresponding to a tangent function or exponentially or also according to other suitable functions. In this regard the increase R can also take into account a desired density of an achieved coverage of the k-space. The increase R can be selected in particular depending on a desired coverage of the k-space by means of the k-space trajectories developed by means of the additional gradients GZ, GZ', GZ", GZ''' used.

Figure 4:
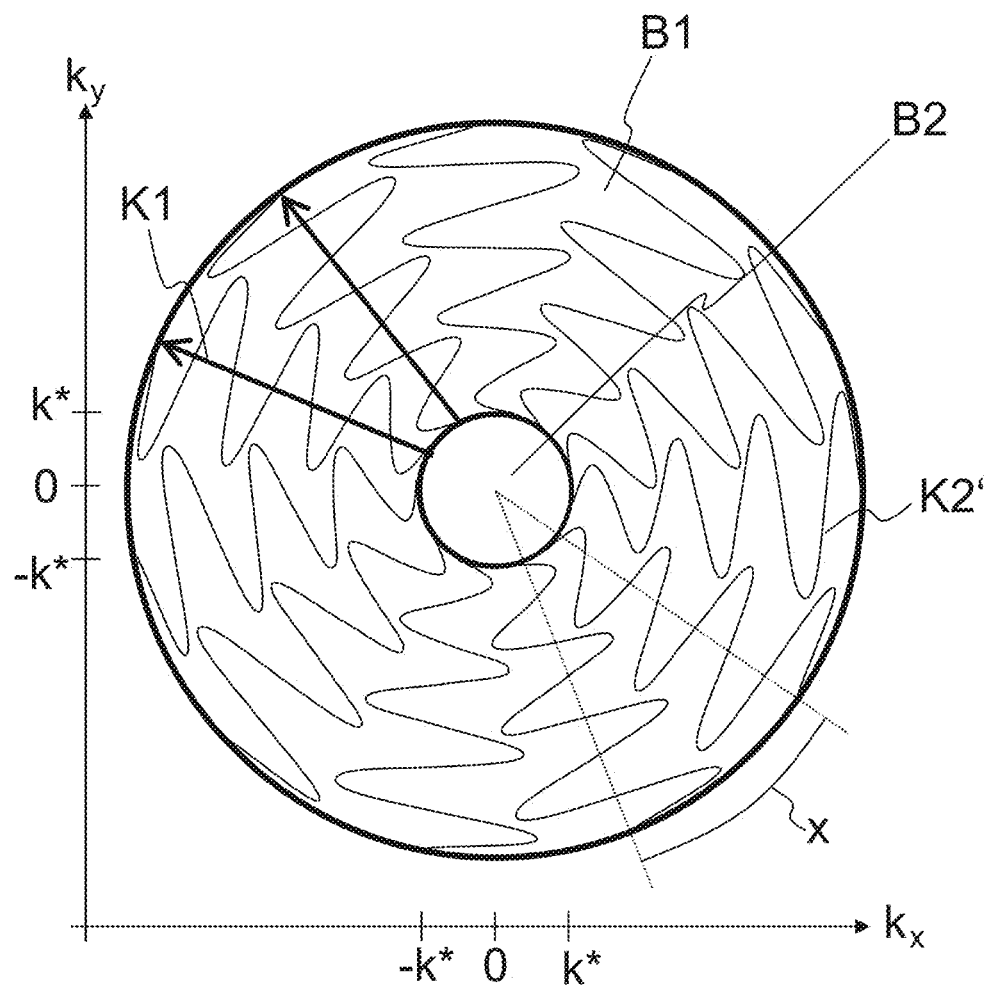
FIG. 4 shows a schematic representation of a further example of an acquisition scheme of scan data in the k-space in accordance with aspects of the disclosure.

For instance, in the $G_{ry}$ direction and in the $G_{rz}$ direction gradients GZ" and GZ''' can be switched according to the following equations:

$$k_{ry}(t) = \tan(x/2) t * A_{max} * \sin(\overline{\omega}t),$$

$$k_{rz}(t) = \tan(x/2) t * A_{max} * \cos(\overline{\omega}t),$$

wherein t represents the time and thus the distance from the k-space center, and x is e.g. a variable dependent on a density of the scanned k-space trajectories, e.g. the angle between the center lines, which run in the interior of a k-space trajectory scanned by means of the switched gradients, of adjacent k-space trajectories of this type (see also FIG. 4). The amplitude is therefore increased in a linearly fanned manner with a size (here tan(x/2) which is dependent on the density with which scanned k-space trajectories lie adjacent to one another. In this way, a uniform coverage is achieved on the one hand with a constant x, and on the other hand the amplitude is particularly favorable for the density of the various k-space scanned trajectories used, as a result of which a scanning which is particularly good overall is achieved.

If only one additional gradient GZ, GZ', GZ" or GZ''' or two additional gradients e.g. GZ and GZ' or GZ" and GZ''' is/are switched with the same phasing and same modulation (not shown), the k-space trajectory of the modulation which is passed through during the recording of the scan data is deflected accordingly from the gradient direction $G_r$, e.g. in a wavelike manner, in a plane defined by the gradient direction $G_r$ and the directions $G_{ry}$ and/or $G_{rz}$, in which additional gradients GZ, GZ', GZ" or GZ''' are switched. The modulation of the amplitude of an additional gradient GZ, GZ' can be sinusoidal, for instance, as shown. A sinusoidal modulation results in a uniform, periodic variation in the amplitude, which can be calculated and generated effectively.

If two additional gradients GZ and GZ' are switched with a different phasing or different modulation, the k-space trajectory which is passed through during the recording of the scan data will run around the gradient direction $G_r$, e.g. in a helical (if possible elliptical) manner, in accordance with the modulation or modulations.

Figure 3:
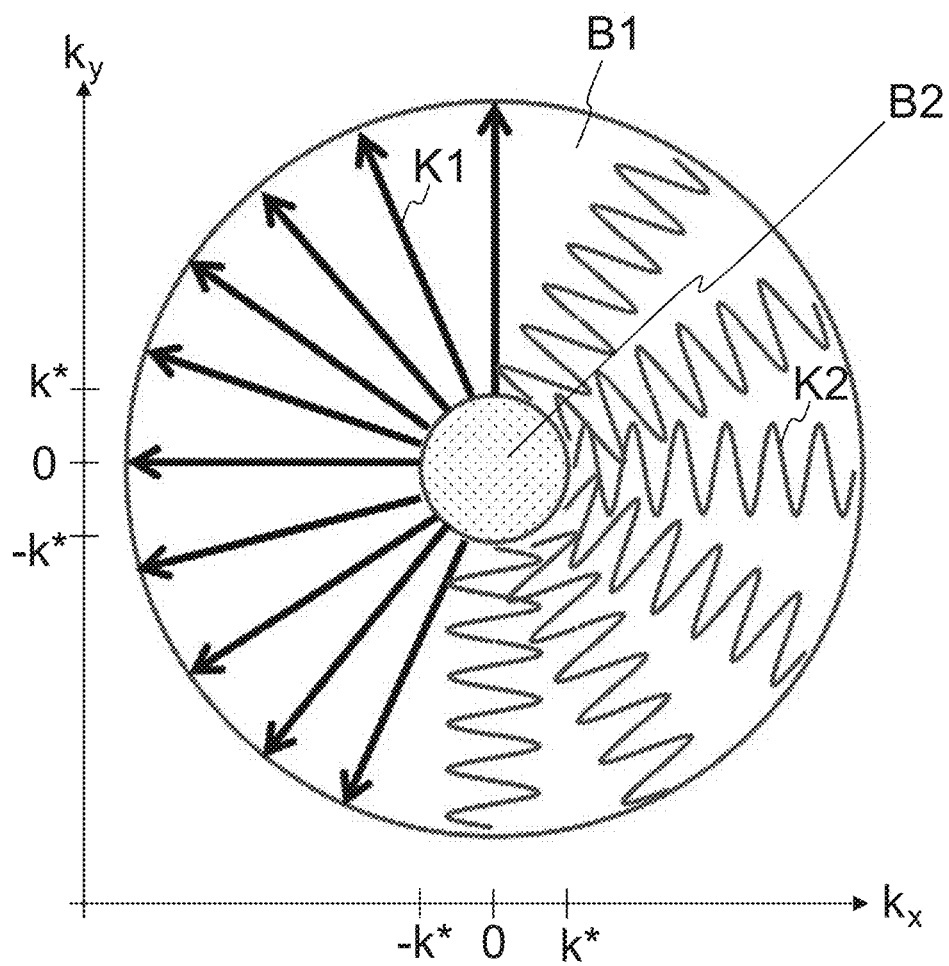
FIG. 3 shows a schematic representation of an example of an acquisition scheme of scan data in the k-space in accordance with aspects of the disclosure.

FIG. 3 shows a schematic representation of an example of an acquisition scheme of scan data in the k-space. The k-space values in the first region B1 which can be read out by means of a sequence according to FIG. 2, for instance, only start with a k-space value k* which depends on the strength of the current gradients and in particular on the echo time t1. Here k=t1*G applies, with G being the strength (amplitude) of the gradient.

The scanning scheme shown in FIG. 3 can be a two-dimensional scanning scheme, e.g. in the ky-kx plane (as shown), or also a three-dimensional scanning scheme which extends analogously in the shape of a cone about the k-space center. In FIG. 3, k-space trajectories of a first type K1 and k-space trajectories of a second type K2 are shown in a first region B1, which extends in the k-space between a minimum radius of k* as far as a radius of a maximum k-space value (outer edge B1) about the k-space center.

The k-space trajectories of the first type K1 run radially outward on radial half radii from the k-space point which is remote from the k-space center in the direction of the respectively switched constant gradient Gr k*. When the scan data is recorded along one of the k-space trajectories of the first type K1, no additional gradients were switched.

k-space trajectories of the second type K2 likewise run from a k* of the k-space point remote from the k-space center as far as the outer edge of the first region B1, but not on a radial k-space trajectory, but instead on a k-space trajectory modulated according to the switched additional gradients. For the association between the switched additional gradients and course of the k-space trajectory, reference is made to the embodiments already made with reference to FIG. 2. The k-space trajectories of the second type K2 shown in FIG. 3 can be generated in particular by means of additional gradients GZ and/or GZ' according to FIG. 2.

It is apparent that the k-space with a k-space trajectory of the second type K2 is scanned with a higher coverage than with a k-space trajectory of the first type K1. In the example shown in FIG. 3, approximately half of the first region B1 is covered with k-space trajectories of the first type K1 and the other half is covered with k-space trajectories of the second type K2. As a result of the shape of the k-space trajectories of the second type K2 which are deflected as a function of the maximum amplitudes of the switched additional gradients, a lower number of k-space trajectories of the second type K2 is required to achieve a similar coverage of the k-space than k-space trajectories of the first type K1 would need. It is conceivable, with each recording of scan data in the first region B1, to switch additional gradients, so that in the first region B1 only k-space trajectories of the second type K2 are scanned. It is also conceivable for scan data to be recorded for at least one k-space trajectory of the second type K2, along which scan data is recorded, also along a k-space trajectory of the first type K1 with the same constant gradients $G_x$, so that the scan data along the k-space trajectory of the first type K1 in the k-space lies in the interior of the k-space trajectory of the second type K2. The entire first region B1 can also be scanned by such pairs of k-space trajectories of the first and the second type K1 and K2 with in each case the same constant gradients $G_x$.

k-space points in the k-space center could only be acquired with a sequence, as shown in FIG. 2, if the time t1 went toward zero since the constant gradient has already reached its full strength before irradiating the HF excitation pulse. However, this is not generally possible in real systems, so that scan data in the second region B2 comprising the k-space center, said second region corresponding to the region which covers the k-space corresponding to the mapping area, which is not covered by the first region B1 of the k-space, is different to that in the first region B1. For instance, scan points in the second region B2 can be described as in conjunction with FIG. 1, block 209, e.g. point by point by means of single point imaging methods on a Cartesian k-space grid or in another known manner. It is essentially also conceivable for scan data which lie in the k-space in the second region B2 to record these on radial k-space trajectories.

In the example shown in FIG. 3, the k-space trajectories of the second type lie in an associated subregion of the first region B1. This can be achieved by, during recordings of scan data, additional gradients being switched in gradient directions $G_r$ corresponding to an associated subregion of the first region. In this way, the reconstruction of image data from the scan data recorded in the k-space can likewise take place region by region at least in substeps.

It is also conceivable, however, to arrange k-space trajectories of the first type K1 and k-space trajectories of the second type K2 in a uniformly distributed manner in the first region, by additional gradients being switched in uniformly distributed gradient directions $G_r$ during recordings of scan data.

FIG. 4 shows a schematic representation of a further example of an acquisition scheme of scan data in the k-space. The same reference characters correspond to the reference characters used in FIG. 3.

The scanning scheme shown in FIG. 4 can in turn be a two-dimensional scanning scheme, e.g. in the ky-kx plane (as shown), or also a three-dimensional scanning scheme, which extends in a similarly conical manner about the k-space center. In FIG. 4, k-space trajectories of a first type K1 and k-space trajectories of a second type K2' are shown again in a first region B1, which extends about the k-space center in the k-space between a minimum radius of k* as far as a radius of a maximum k-space value (outer edge B1).

The k-space trajectories of the first type K1 again run radially outward on radial half radii from the k-space point remote from the k-space center in the direction of the respectively switched constant gradient $G_r$ k*. No additional gradients were switched when scan data is recorded along one of the k-space trajectories of the first type K1.

The k-space trajectories of the second type K2' shown in FIG. 4 likewise run from a k* of the k-space point remote from the k-space center as far as the outer edge of the first region B1, but not on a radial k-space trajectory, but instead on a k-space trajectory which is modulated according to the switched additional gradients. The k-space trajectories of the second type K2' shown in FIG. 4 have been generated with additional gradients contrary to the k-space trajectories of the second type K2 shown in FIG. 3, which in addition to a modulation have an increase in the amplitude with an increasing distance from the k-space center. For instance, the k-space trajectories of the second type K2 shown in FIG. 4 can be generated by means of additional gradients GZ" and/or GZ''' according to FIG. 2.

It is apparent that the k-space with a k-space trajectory of the second type K2' is scanned with a higher coverage than with a k-space trajectory of the first type K1 and even than with k-space trajectories of the second type K2 according to FIG. 3.

In the example shown in FIG. 4, by way of example the entire region B1 is covered with k-space trajectories of the second type K2', wherein an angle x is present between two center lines, which run in the interior of a k-space trajectory of the second type K2', from adjacent k-space trajectories of the second type K2'. For a uniform distribution of k-space lines of the second type, the angle x can be selected to be the same for all used pairs of k-space trajectories of the second type K2'. For two of the k-space trajectories of the second type K2' shown, by way of example k-space trajectories of the first type K1 are additionally also shown, which lie in the k-space in the interior of the associated k-space trajectory of the second type K2'.

That said with reference to FIG. 3 applies analogously to FIG. 4 up to the embodiment of the k-space trajectories of the second type K2'.

Figure 5:
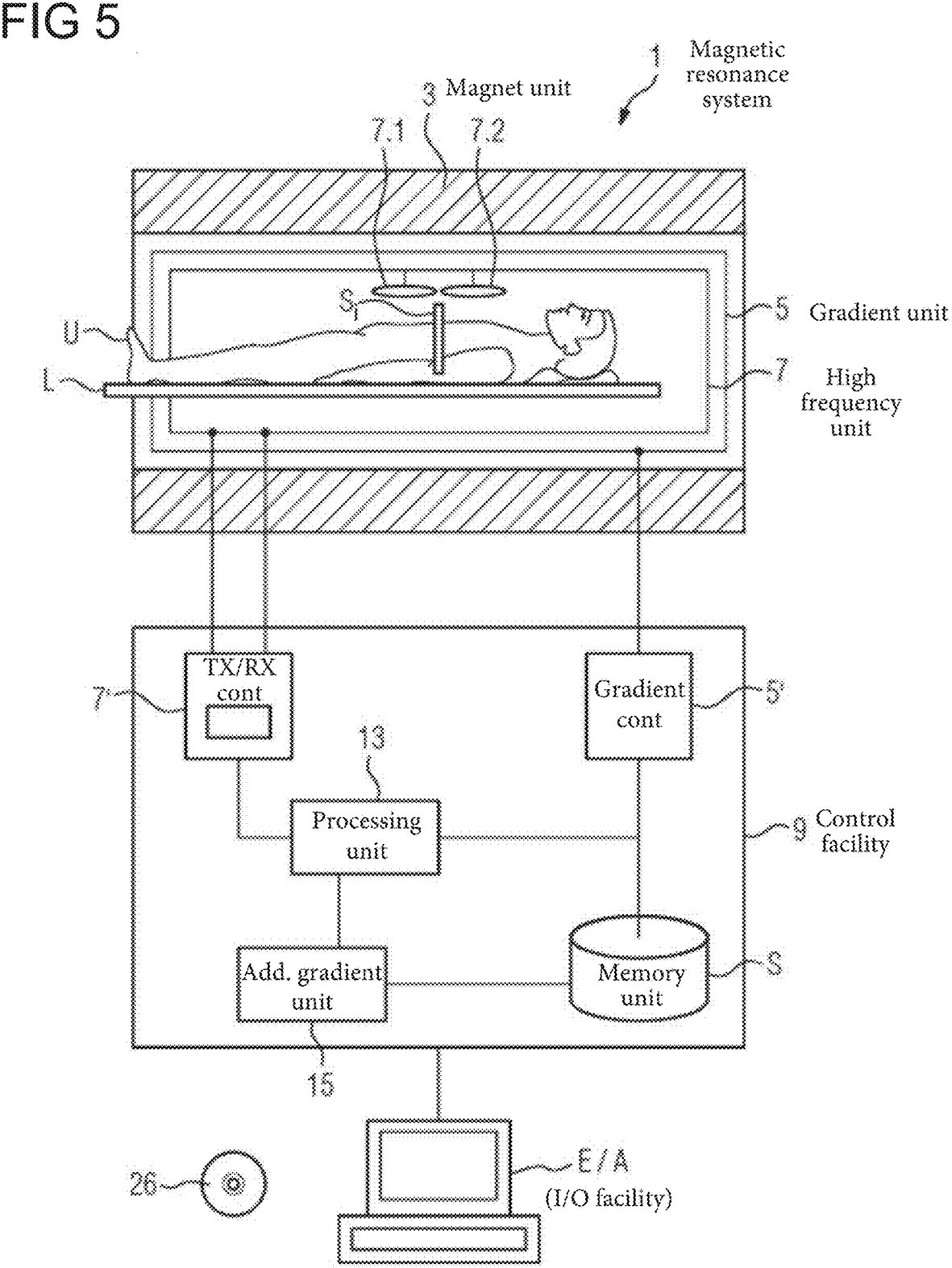
FIG. 5 shows a schematically shown magnetic resonance system in accordance with aspects of the disclosure.

FIG. 5 shows a schematic representation of a magnetic resonance system 1. This comprises a magnet unit 3 for generating the main magnetic field, a gradient unit 5 for generating the gradient fields, a high frequency unit 7 for irradiating and receiving high frequency signals and a control facility 9 embodied to carry out a method.

In FIG. 5, these sub-units of the magnetic resonance system 1 are only shown roughly schematically. In particular, the high frequency unit 7 may consist of a plurality of sub-units, for instance of a plurality of coils such as the coils 7.1 and 7.2 shown schematically or more coils, which may either be designed solely to transmit high frequency signals or solely to receive the induced high frequency signals, or be designed to do both.

In order to examine an examination object U, for example a patient or else a phantom, this can be introduced into the magnetic resonance system 1 into the measurement volume thereof on a couch L. The slice $S_i$ represents an example target volume of the examination object from which data is meant to be recorded and thus acquired.

The control facility 9 is used to control the magnetic resonance system 1 and in particular can control the gradient unit 5 by means of a gradient controller 5' and can control the high frequency unit 7 by means of a high frequency transmit/receive controller 7'. The high frequency unit 7 can here comprise a plurality of channels on which signals can be transmitted or received.

The high frequency unit 7 together with its high frequency transmit/receive controller 7' is responsible for generating and radiating (transmitting) an alternating high frequency field for manipulating the spins in a region to be manipulated (for instance in slices $S_i$ to be measured) of the examination object U. The center frequency of said alternating high frequency field, also referred to as the B1 field, is generally adjusted as much as possible to lie close to the resonant frequency of the spins to be manipulated. Off-resonance refers to deviations of the center frequency from the resonant frequency. In order to generate the B1 field, currents are applied to the HF coils, which currents are controlled in the high frequency unit 7 by the high frequency transmit/receive controller 7'.

Furthermore, the control facility 9 comprises an additional gradient unit 15, with which in accordance with the disclosure additional gradients can be determined, which can be implemented by the gradient controller 5'. The control facility 9 is overall embodied to carry out a method.

A processing unit 13 included in the control facility 9 is designed to perform all the processing operations needed for the required measurements and determinations. Intermediate results and results required for this purpose or determined in this process can be saved in a memory unit S of the control facility 9. The units shown need not necessarily be interpreted here as physically separate units but merely constitute a subdivision into logical units, which, however, can also be implemented e.g. in fewer physical units or even in just one physical unit.

Via an input/output facility E/A of the magnetic resonance system 1 it is possible e.g. for a user, to direct control commands to the magnetic resonance system and/or to display results from the control facility 9, such as e.g. image data.

A method described here can also exist in the form of a computer program product, which comprises a program and implements the described method on a control facility 9 when it is executed in the control facility 9. Likewise there can also be an electronically readable data storage medium 26 comprising electronically readable control information stored thereon, which information comprises at least one such computer program product as just described and is designed such that it performs the described method when the data storage medium 26 is used in a control facility 9 of a magnetic resonance system 1.

The invention claimed is:

1. A method for producing scan data from an examination object, the method comprising:
    reading out a k-space which corresponds to a mapping area of the scan data, by:
    a) switching a constant gradient using a gradient field generator of a magnetic resonance system;
    b) irradiating an RF excitation pulse using an RF transmitter/receiver of the magnetic resonance system;
    c) following a time t1 after the last irradiated RF excitation pulse, recording echo signals using the RF transmitter/receiver; and
    d) storing the recorded echo signals as scan data along a trajectory in k-space predetermined by a strength of the switched gradient,
    wherein the steps a) to d) are carried out repeatedly with various switched constant gradients, and the various gradients are switched in at least two phase encoding directions, and
    wherein at least once following the time t1 after the last switched RF excitation pulse, additional gradients with a modulating amplitude are switched in at least one direction which is oriented at right angles to a direction predetermined by the already switched constant gradients, until the k-space corresponding to the mapping area is read out in a first region which depends on the time t1; and
    e) reading out the k-space corresponding to the mapping area, which is not covered by the first region of the k-space and which comprises at least a k-space center, differently to that described by steps a) to d), and storing this scan data; and
    reconstructing image data from the stored scan data of the k-space using a control facility of the magnetic resonance system.

2. The method as claimed in claim 1, wherein the irradiated RF excitation pulses are irradiated after full strength of the constant gradients is reached.

3. The method as claimed in claim 1, wherein the irradiated RF excitation pulses are non-slice-selective RF excitation pulses.

4. The method as claimed in claim 1, wherein the scan data is read out in step e) as Cartesian scan data using a single point imaging method.

5. The method as claimed in claim 1, wherein a modulation of the amplitude of an additional gradient is sinusoidal.

6. The method as claimed in claim 1, wherein a maximum amplitude of the modulation of the additional gradients is selected as a function of a desired coverage of the k-space.

7. The method as claimed in claim 1, wherein a portion of the first region is predetermined, in which additional gradients are switched while scan data is recorded.

8. The method as claimed in claim 7, wherein the portion of the first region, in which additional gradients are switched while scan data is recorded as a function of a permissible noise development and/or is defined as a function of a desired maximum scan time for storing all scan data of the first region and/or as a function of a desired k-space coverage.

9. The method as claimed in claim 1, wherein additional gradients are switched during recordings of scan data in an associated subregion of the first region or equally distributed in the first region.

10. The method as claimed in claim 1, wherein additional gradients are switched during each recording of scan data.

11. The method as claimed in claim 1, wherein the amplitude of an additional gradient is increased with increased distance from the k-space center.

12. A magnetic resonance system, comprising:
    a magnet;
    a gradient field generator;
    a high frequency transmitter/receiver; and
    a control facility with a high frequency transmitter/receiver controller with an additional gradient field generator,
    wherein the control facility is embodied to carry out the method as claimed in claim 1 on the magnetic resonance system.

13. A non-transitory computer-readable medium comprising program code which when executed by a control facility of a magnetic resonance system performs the method of claim 1.

* * * * *